United States Patent
Huang et al.

(10) Patent No.: US 11,514,573 B2
(45) Date of Patent: Nov. 29, 2022

(54) ESTIMATING OBJECT THICKNESS WITH NEURAL NETWORKS

(71) Applicant: SHANGHAI UNITED IMAGING INTELLIGENCE CO., LTD., Shanghai (CN)

(72) Inventors: Qiaoying Huang, Edison, NJ (US); Shanhui Sun, Lexington, MA (US); Zhang Chen, Brookline, MA (US); Terrence Chen, Lexington, MA (US)

(73) Assignee: SHANGHAI UNITED IMAGING INTELLIGENCE CO., LTD., Shanghai (CN)

( * ) Notice: Subject to any disclaimer, the term of this patent is extended or adjusted under 35 U.S.C. 154(b) by 156 days.

(21) Appl. No.: 17/014,573

(22) Filed: Sep. 8, 2020

(65) Prior Publication Data

US 2021/0158510 A1 May 27, 2021

Related U.S. Application Data

(60) Provisional application No. 62/941,198, filed on Nov. 27, 2019.

(51) Int. Cl.
*G06T 7/00* (2017.01)
*G06T 7/11* (2017.01)
(Continued)

(52) U.S. Cl.
CPC .......... *G06T 7/0012* (2013.01); *A61B 5/0044* (2013.01); *A61B 5/1128* (2013.01);
(Continued)

(58) Field of Classification Search
CPC ... G06T 7/0012; G06T 3/0093; G06T 7/0014; G06T 7/11; G06T 7/248; G06T 7/55; G06T 7/73; G06T 11/206; G06T 13/80; G06T 19/00; G06T 2200/24; G06T 2207/10016; G06T 2207/20081; G06T 2207/20084; G06T 2207/30048; G06T 2210/41; G06T 2207/10072; G06T 7/12; G06T 7/62;
(Continued)

(56) References Cited

PUBLICATIONS

Xue et al. "Direct Estimation of Regional Wall Thicknesses via Residual Recurrent Neural Network." arXiv: 1705.009728v1 [cs.CV] May 26, 2017, 13 pages (Year: 2017).*

(Continued)

*Primary Examiner* — Jon Chang
(74) *Attorney, Agent, or Firm* — Zhong Law, LLC

(57) ABSTRACT

Described herein are neural network-based systems, methods and instrumentalities associated with estimating a thickness of an anatomical structure based on a visual representation of the anatomical structure and a machine-learned thickness prediction model. The visual representation may include an image or a segmentation mask of the anatomical structure. The thickness prediction model may be learned based on ground truth information derived by applying a partial differential equation such as Laplace's equation to the visual representation and solving the partial differential equation. When the visual representation includes an image of the anatomical structure, the systems, methods and instrumentalities described herein may also be capable of generating a segmentation mask of the anatomical structure based on the image.

18 Claims, 11 Drawing Sheets

(51) Int. Cl.

| | | |
|---|---|---|
| *G06T 7/55* | (2017.01) | |
| *G06K 9/62* | (2022.01) | |
| *G06N 3/04* | (2006.01) | |
| *G16H 50/50* | (2018.01) | |
| *G16H 50/30* | (2018.01) | |
| *G16H 30/40* | (2018.01) | |
| *G06F 3/0485* | (2022.01) | |
| *G06T 11/20* | (2006.01) | |
| *G06T 13/80* | (2011.01) | |
| *G06T 19/00* | (2011.01) | |
| *G06T 7/73* | (2017.01) | |
| *G06T 7/246* | (2017.01) | |
| *A61B 5/00* | (2006.01) | |
| *A61B 5/11* | (2006.01) | |
| *G06T 3/00* | (2006.01) | |
| *G06N 3/08* | (2006.01) | |

(52) U.S. Cl.
CPC .......... *A61B 5/7264* (2013.01); *G06F 3/0485* (2013.01); *G06K 9/6267* (2013.01); *G06N 3/0454* (2013.01); *G06N 3/08* (2013.01); *G06T 3/0093* (2013.01); *G06T 7/0014* (2013.01); *G06T 7/11* (2017.01); *G06T 7/248* (2017.01); *G06T 7/55* (2017.01); *G06T 7/73* (2017.01); *G06T 11/206* (2013.01); *G06T 13/80* (2013.01); *G06T 19/00* (2013.01); *G16H 30/40* (2018.01); *G16H 50/30* (2018.01); *G16H 50/50* (2018.01); *G06T 2200/24* (2013.01); *G06T 2207/10016* (2013.01); *G06T 2207/20081* (2013.01); *G06T 2207/20084* (2013.01); *G06T 2207/30048* (2013.01); *G06T 2210/41* (2013.01)

(58) Field of Classification Search
CPC ... A61B 5/0044; A61B 5/1128; A61B 5/7264; G06F 3/0485; G06K 9/6267; G06K 9/6271; G06N 3/0454; G06N 3/08; G06N 3/0445; G06N 3/084; G16H 30/40; G16H 50/30; G16H 50/50; G16H 50/20; G06V 2201/03; G06V 10/454; G06V 10/82
See application file for complete search history.

(56) References Cited

PUBLICATIONS

Jones, Stephen E. et al.; "Three-Dimensional Mapping of Cortical Thickness Using Laplace's Equation," Human Brain Mapping, vol. 11, pp. 12-32 (2000).

Yezzi Jr., Anthony J. et al.; "An Eulerian PDE Approach for Computing Tissue Thickness," IEEE Transactions on Medical Imaging, vol. 22, No. 10, pp. 1332-1339 (Oct. 2003).

Khalifa, Fahmi et al.; "Accurate Automatic Analysis of Cardiac Cine Images," IEEE Transactions on Biomedical Engineering, vol. 59, No. 2, pp. 445-455 (Feb. 2012).

Prasad, M. et al.; "Myocardial wall thickening from gated Magnetic Resonance images using Laplace's equation," Proc SPIE Int Soc Opt Eng. (Feb. 2009).

* cited by examiner

ESTIMATING OBJECT THICKNESS WITH NEURAL NETWORKS

CROSS-REFERENCE TO RELATED APPLICATIONS

This application claims the benefit of Provisional U.S. Patent Application No. 62/941,198, filed Nov. 27, 2019, the disclosure of which is incorporated herein by reference in its entirety.

BACKGROUND

Image-based organ or tissue thickness estimation plays a critical role in medical diagnosis and treatment. Taking myocardial diseases assessment as an example, the thickness of the heart muscle (e.g., myocardium) can serve as a good indicator of myocardium dysfunction, even without a full motion analysis of the heart. For instance, the heart muscle may become abnormally thin for patients having myocardial infarction diseases and abnormally thick for patients having hypertrophic cardiomyopathy. In other examples, the thickness of gray matter in the human cerebral cortex has been used to diagnose Alzheimer's disease and other neurodegenerative disorders, and the thickening of the tibial cartilage has been linked to osteoarthritis. Hence, having the ability to accurately estimate the thickness of an anatomical object in the human can significantly increase the success rate of clinical practice.

Conventional thickness estimation systems rely heavily on constructing mathematical models of the relevant anatomical structure and calculating the thickness of the anatomical structure in real time by solving various equations or performing different transformations based on the mathematical models. These systems are computationally expensive, time consuming, and error prone. Hence, it is desirable to utilize modern technologies such as computer vision and machine learning technologies to improve the efficiency, speed, and accuracy of thickness estimation.

SUMMARY

Described herein are neural network-based systems, methods and instrumentalities associated with thickness estimation. A system as described herein may comprise one or more processors and one or more storage devices, the one or more storage devices configured to store instructions that, when executed by the one or more processors, cause the one or more processors to receive a visual representation of an anatomical structure (e.g., a myocardium, a cortex, a cartilage, etc.), extract a plurality of features from the visual representation, and predict a thickness of the anatomical structure using a machine-learned prediction model that maps the thickness of the anatomical structure to the plurality of extracted features. The prediction model may be learned using a neural network (e.g., which may be implemented by the one or more processors) and based on ground truth information derived using a partial differential equation such as Laplace's equation. The learning (e.g., the training of the neural network) may comprise the neural network receiving a training image or a training segmentation mask associated with the anatomical structure, predicting a first thickness of the anatomical structure based on features extracted from the training image or the training segmentation mask, comparing the first predicted thickness with a ground truth thickness, and adjusting one or more neural network parameters based on a difference between the first predicted thickness and the ground truth thickness. In embodiments, the learning may also comprise the neural network receiving a rotated version of the training image or training segmentation mask, predicting a second thickness of the anatomical structure based on features extracted from the rotated version of the training image or training segmentation mask, obtaining a rotated version the ground truth thickness, comparing the second predicted thickness with the rotated version of the ground truth thickness, and adjusting the network's parameters based on a difference between the second predicted thickness and the rotated version of the ground truth.

In embodiments, the visual representation of the anatomical structure described herein may comprise a two-dimensional (2D) and/or a three-dimensional (3D) visual representation of the anatomical structure. The visual representation may comprise an image depicting the anatomical structure or a segmentation mask of the anatomical structure. When the visual representation comprises an image of the anatomical structure, the one or more processors may be further configured generate a segmentation mask for the anatomical structure based on the plurality of features extracted from the image depicting the anatomical structure. The one or more processors may implement a neural network pre-trained to perform this task and the pre-training of the neural network may comprise the neural network receiving a training image depicting the anatomical structure, the neural network generating an estimated segmentation mask for the anatomical structure based on features extracted from the training image, the neural network providing the estimated segmentation mask to a pre-trained thickness prediction network to obtain a first estimated thickness of the anatomical structure, the neural network generating a second estimated thickness of the anatomical structure based on at least a subset of the features extracted from the training image, and the neural network adjusting its parameters based on a loss function associated with the first estimated thickness and second estimated thickness.

In embodiments, the one or more processors may be configured to implement a first neural network pre-trained to generate a segmentation mask for the anatomical structure and implement a second neural network pre-trained to predict a thickness of the anatomical structure. The first and second neural networks may be trained together (e.g., in an end-to-end manner). During the training, the first neural network may generate an estimated segmentation mask for the anatomical structure based on features extracted from a training image and provide the estimated segmentation mask to a pre-trained thickness prediction network to obtain a first estimated thickness of the anatomical structure. The second neural network may generate a second estimated thickness of the anatomical structure based on the estimated segmentation mask, and the first and second neural networks may adjust their respective parameters based on a loss function associated with the first estimated thickness and the second estimated thickness.

In embodiments, the visual representation of the anatomical structure may comprise a time-based sequence of images or segmentation masks associated with the anatomical structure and the one or more processors may be configured to implement a neural network pre-trained to predict the thickness of the anatomical structure based on the time-based sequence of images or segmentation masks. For example, the training of the neural network may comprise the neural network predicting a first thickness of the anatomical structure corresponding to a first image or a first segmentation mask and the neural network predicting a second thickness of the anatomical structure corresponding to a second image or a second segmentation mask that is sequential in time to the first image or first segmentation mask, where the second thickness is predicted based on a temporal correlation between the first and second images or between the first and second segmentation masks. The neural network may comprise a recurrent neural network configured to encode the temporal correlation between the first and second images or between the first and second segmentation masks.

BRIEF DESCRIPTION OF THE DRAWINGS

A more detailed understanding of the examples disclosed herein may be obtained from the following description, given by way of example in conjunction with the accompanying drawing.

DETAILED DESCRIPTION

The present disclosure is illustrated by way of example, and not by way of limitation, in the figures of the accompanying drawings.

Figure 1A:
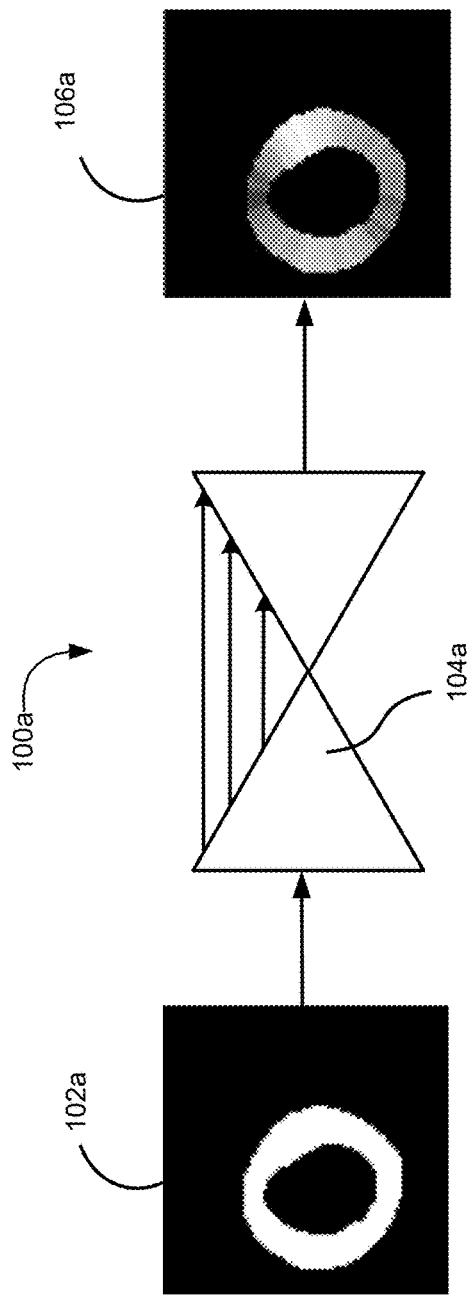
FIGS. 1A and 1B are simplified block diagrams illustrating example neural network systems for estimating the thickness of an anatomical structure based on a visual representation of the anatomical structure.
Figure 1B:
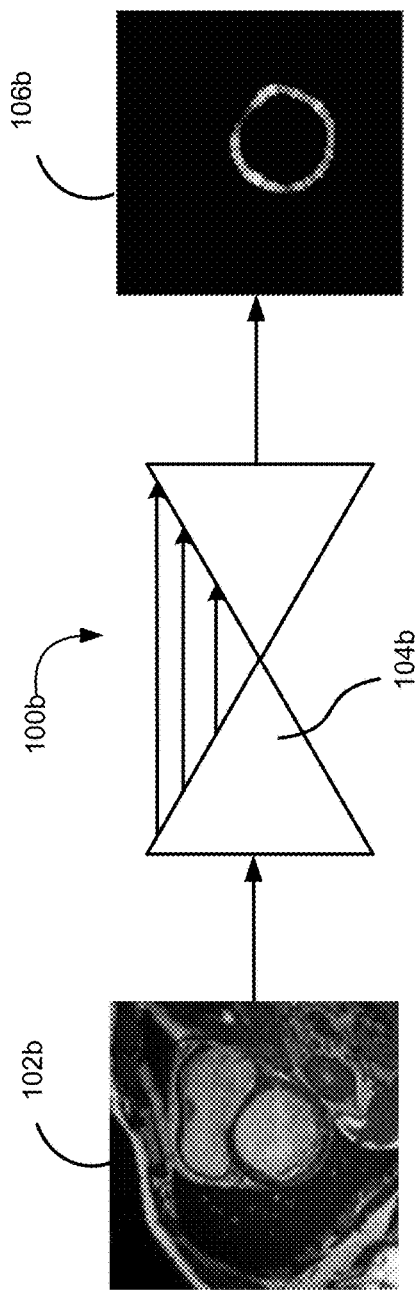

FIG. 1A and FIG. 1B are block diagrams illustrating example neural network systems 100a and 100b for estimating the thickness of an anatomical structure (e.g., an anatomical object) based on one or more visual representations of the anatomical structure. The anatomical structure may be any organ or tissue of the human body including, for example, the myocardium, the cortex, knee cartilage, blood vessels, etc., and the one or more visual representations may comprise a segmentation 102a (e.g., a binary segmentation mask) of the anatomical structure or an image 102b (e.g., a medical scan) of the anatomical structure. The thickness estimation may be performed using artificial neural networks (ANNs) 104a and/or 104b each of which may include a convolutional neural network (CNN) trained (e.g., pre-trained) to receive the respective visual representations (e.g., the segmentation 102a and/or image 102b) and predict the thickness of the anatomical structure based on features extracted from the respective visual representations. The prediction may be made, for example, based on respective machine-learned thickness prediction models that map the thickness of the anatomical structure to specific visual features identified in the segmentation 102a and image 102b. As a result of the prediction, the neural network systems 100a and 100b (e.g., the ANNs 104a and 104b) may generate respective indications 106a and 106b of the thickness of the anatomical structure at one or more pixel positions (e.g., at each pixel position) of the segmentation 102a and image 102b. The indications 106a and/or 106b may be provided in various forms. For example, the indications may include numerical values that indicate the thickness of the anatomical structure at the one or more pixel positions and/or color-coded or shaded versions (e.g., thickness maps) of the segmentation 102a and/or image 102b in which areas (e.g., pixels) having different thickness are distinguished by respective colors or shades, as illustrated in FIGS. 1A and 1B.

The ANNs 104a and/or 104b may be configured and trained (e.g., pre-trained) to learn the thickness prediction models described herein, for example, via a machine-learning or training process. Each of the ANNs 104a and 104b may include a plurality of layers such as one or more input layers, one or more hidden layers, and/or one or more output layers. The input layers may be configured to receive the segmentation 102a and/or image 102b and pass them to subsequent layers for processing. Each of the input layers may include one or more channels and each channel may be configured to receive data from a respective source (e.g., three channels if the input visual representation includes an RGB image). The hidden layers may include one or more convolutional layers and/or one or more pooling layers configured to acquire feature maps of the segmentation 102a or image 102b. For example, each of the convolutional layers may include a plurality of kernels or filters that, when applied to the input visual representation (e.g., the segmentation 102a or image 102b), identify keypoints in the visual representation that collectively represent a feature or pattern of the visual representation. The convolution operation may be followed by batch normalization and/or activation (e.g., using a rectified linear unit (ReLU) function), and the features extracted by the convolutional layers (e.g., in the form of one or more feature maps) may be down-sampled through the one or more pooling layers (e.g., using a 2×2 window and a stride of 2) to reduce the redundancy and/or dimension of the features (e.g., by a factor of 2). Subsequently, the down-sampled features may go through an up-sampling process via transpose convolution operation (e.g., using 3×3 transposed convolutional kernels with a stride of 2) to recover the spatial details of the visual representation. One or more dense feature maps (e.g., up-scaled by a factor of 2) may obtained as a result of the up-sampling operation and the feature maps may be provided to a regression layer (e.g., a fully-connected convolutional layer with a non-linear activation function) to estimate continuous thickness values of the anatomical structure at one or more pixel positions. The estimated thickness values may then be used to render the thickness indications 106a and/or 106b, as shown in FIGS. 1A and 1B.

The ANNs 104a and/or 104b may acquire (e.g., learn) their respective operating parameters such as the weights associated with the filters described above through a training process. The training may be conducted using images and/or segmentation masks of the anatomical structure that are synthesized (e.g., computer-simulated or computer-generated) and/or obtained from medical scans of the anatomical structure such as magnetic resonance imaging (MRI), X-Ray scans, computer tomography (CT) scans, positron emission tomography (PET) scans, etc. For example, from a set of medical scan images, corresponding segmentation masks may be derived via annotation and/or suitable image processing and analysis techniques such as that disclosed in commonly assigned U.S. patent application Ser. No. 16/905, 115, filed Jun. 18, 2020, entitled "Systems and Methods for Image Segmentation," the disclosure of which is hereby incorporated by reference in its entirety.

Figure 2:
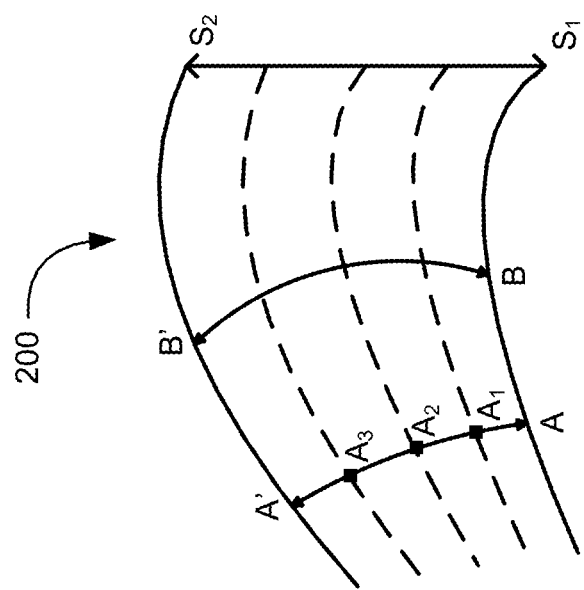
FIG. 2 is a simplified block diagram illustrating an example of using Laplace's equation to derive ground truth associated with the thickness of an anatomical structure.

The training of the ANNs 104a and/or 104b may utilize ground truth derived using a partial differential equation (PDE) such as Laplace's equation. FIG. 2 is a diagram showing an example of how Laplace's equation may be used to derive the ground truth for the thickness of an anatomical structure depicted in a training image or segmentation. The figure shows a two-dimensional (2D) example, but it should be noted that the techniques described herein are also applicable to three-dimensional (3D) use cases and may be applied independent of any specific coordinate system.

Laplace's equation may be a second-order partial differential equation that can be used to capture (e.g., mathematically) the surface or boundary conditions of an anatomical structure as depicted a training image or segmentation. For instance, the equation may be used to compute a scalar field $\psi$ (e.g., representing values of electric potential) enclosed between two boundary contours (e.g., inner and outer boundaries) $S_1$ and $S_2$ of the anatomical structure 200 shown in FIG. 2. The equation may take the following form:

$$\nabla^2 \psi = \frac{\delta^2 \psi}{\delta x^2} + \frac{\delta^2 \psi}{\delta y^2} + \frac{\delta^2 \psi}{\delta z^2} = 0$$

where $\psi$ may be equal to $\psi_1$ on $S_1$ and $\psi_2$ on $S_2$. By solving the equation, a layered set of surfaces (e.g., shown by dashed lines in FIG. 2) may be determined that transition from $S_1$ to $S_2$ and respective values of $\psi$ may be defined for points (e.g., any point) between the two surfaces $S_1$ and $S_2$ such as corresponding surface points A and A' or B and B'. For example, points on the inner contour $S_1$ (e.g., such as points A and B) may be assigned a $\psi$ value of 0 (e.g., in units of volts to indicate electric potential), points on the outer contour $S_2$ (e.g., such as points A' and B') may be assigned a $\psi$ value of 10,000, and points between the two boundary contours (e.g., between A and A' or between B and B') may be assigned respective w values that satisfy $\nabla^2\psi=0$. This way, nonintersecting (e.g., parallel) intermediate lines may be obtained based on Laplace's equation, for example, using the following formula:

$$E = -\nabla \psi$$

and E may be normalized, e.g., based on the following equation, to obtain gradient vectors N that correspond to nested sublayers between $S_1$ to $S_2$:

$$N = E/\|E\|$$

where N may point perpendicularly to the corresponding sublayer.

For simplicity of illustration, FIG. 2 only shows three nested sublayers (e.g., in dashed lines) that may correspond to isopotential values of 2500, 5000, and 7500V. But a skilled person in the art will understand that more nested sublayers may be derived in similar manners and the overall thickness of the anatomical structure between two surface points (e.g., A and A', or B and B') may be determined as the sum of the sublayer thickness. For example, once N is determined, a streamline may be computed by starting at a surface point and integrating N (e.g., using the Euler integration method). As shown in FIG. 2, for example, a streamline may be determined between A and A' through interior points $A_1$, $A_2$ and $A_3$ based on a specific integration step size. And by decreasing the integration step size, more interior points between A and A' may be obtained to form a substantially ideal streamline that connects A and A'. Every point on this streamline may be assigned a same thickness value determined via Laplace's equation and/or the Euler integration method (e.g., $A_1$-$A_3$ may be assigned a same thickness value determined based on A and A', $B_1$-$B_3$ may be assigned a same thickness value determined based on B and B', etc.). As such, by solving Laplace's equation, a thickness value may be determined for every point between the two surfaces of the anatomical structure, inclusively. In addition, since there may be fewer points on the inner contour of the anatomical structure than the outer contour of the anatomical structure (e.g., some areas of the anatomical structure may not be touched by a streamline), further operations may be performed to supplement (e.g., smooth) the thickness calculation described herein. For example, linear interpolation based on calculated thickness values may be applied to derive the thickness of those areas are not touched by a streamline to produce a dense thickness map.

Figure 3:
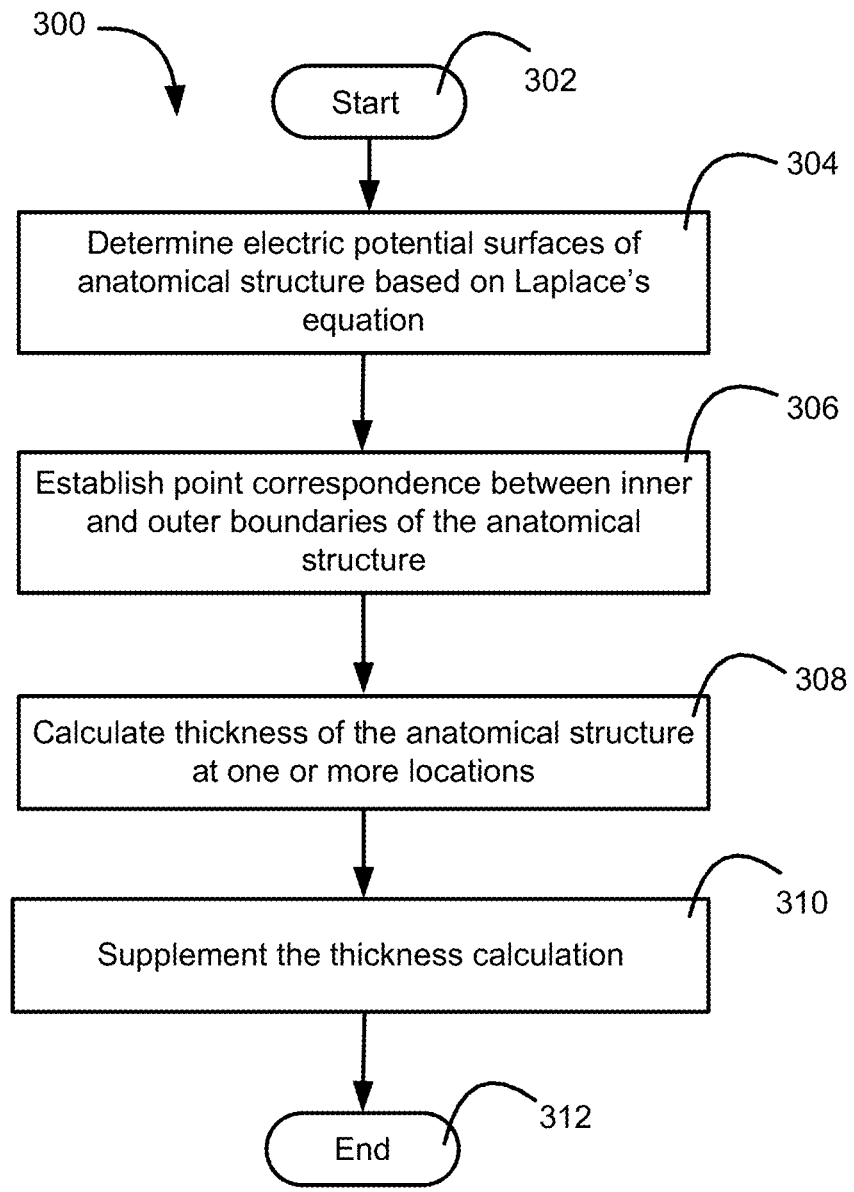
FIG. 3 is a flow diagram of an example process for deriving ground truth of a thickness of an anatomical structure.

FIG. 3 is a flow diagram of an example process 300 for deriving the ground truth associated with the thickness of an anatomical structure such as the myocardium wall. The process 300 may start at 302 and, at 304, surfaces associated with respective electrical potential values may be determined based on Laplace's equation. These surfaces may include, for example, those indicated by dashed lines in FIG. 2 that are located between an inner boundary (e.g., $S_1$ shown in FIG. 2) of the anatomical structure and an outer boundary (e.g., $S_2$ shown in FIG. 2) of the anatomical structure. At 306, correspondence between one or more points on the inner boundary (e.g., points A and B in FIG. 2) and one or more points on the outer boundary (e.g., points A' and B' in FIG. 2) may be established, for example, by determining gradient vectors that are orthogonal to each respective electric potential surface determined at 304 and integrating the vectors, e.g., using the Euler integration method. At 308, thickness of the anatomical structure at one or more locations may be determined based on respective lengths of the streamlines that connect corresponding points of the inner and outer boundaries of the anatomical structure. The thickness calculation may be supplemented at 310, for example, via linear interpolation to smooth out the thickness map generated by the process 300 and the process may then end at 312.

Figure 4:
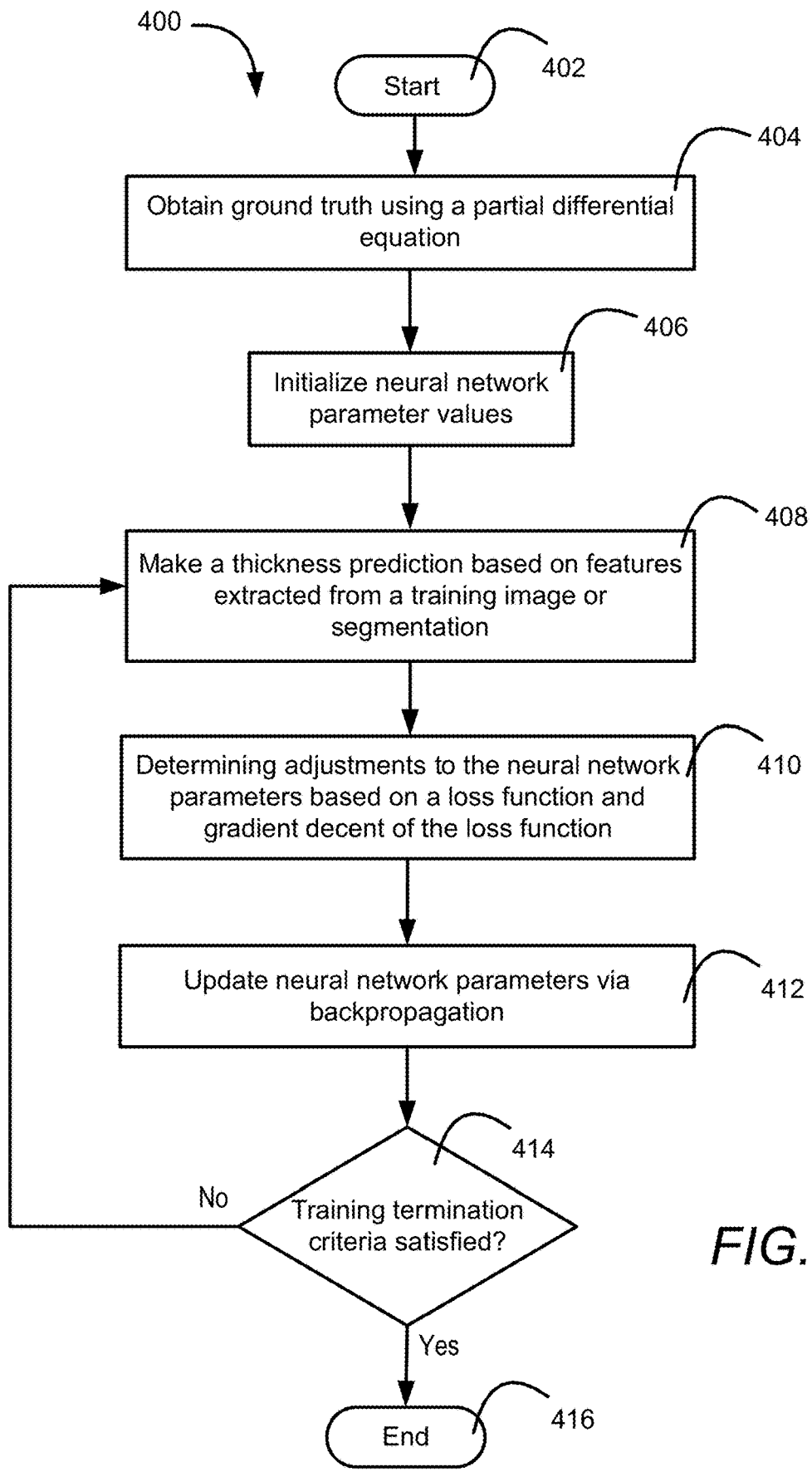
FIG. 4 is a flow diagram illustrating an example neural network training process.

The thickness data derived using the method and process illustrated by FIGS. 2 and 3 may be used as ground truth to train the ANNs 104a and/or 104b to learn the thickness predict models described herein. FIG. 4 is a flow diagram of an example process 400 for training a neural network system (e.g., the neural network systems 100a and/or 100b) to predict the thickness of an anatomical structure based on a visual representation of the anatomical structure. The process 400 may start at 402 and, at 404, ground truth for the thickness of the anatomical structure may be obtained based on a training image or segmentation. As described herein, such ground truth may be derived using a partial differential equation such as Laplace's equation. At 406, the neural network system may initialize its operating parameters such as the weights associated with one or more filters of the neural network system. The parameters may be initialized, for example, based on samples from one or more probability distributions or parameter values of another neural network with a similar architecture. At 408, the neural network system may process the training image or segmentation using the initial filter weights and predict a thickness of the anatomical structure based on features extracted from the training image or segmentation.

At 410, the neural network system may determine adjustments to be made to its operating parameters based on a loss function and a gradient descent (e.g., a stochastic gradient decent) computed to minimize the loss function. In examples, the loss function may be implemented based on a mean squared error (MSE) or an L2 norm distance between the predicted thickness value and the ground truth derived using the partial differential equation. In examples, an L1 norm may be used (e.g., for regularization) with the L2 norm to produce a sparse thickness map (e.g., for the foreground of the input image or segmentation) that may be significantly smaller than a dense thickness map (e.g., for the background of the input image or segmentation). For instance, the background of a thickness map may include many zeros and as such a large area may exist outside the thickness region. By adding a L1 constraint to the prediction process, this characteristic of the thickness map may be taken into consideration during the prediction.

At 412, the neural network system may carry out the adjustments to its current parameter values (e.g., the weights currently assigned to the filters), for example, via a back-propagation process. At 414, the neural network system may determine whether one or more training termination criteria are satisfied. For example, the system may determine that the training termination criteria are satisfied if the system has completed a pre-determined number of training iterations, if the difference between the predicted values and the ground truth values is below a predetermined threshold, or if the change in the value of the loss function between two training iterations falls below a predetermined threshold. If the determination at 414 is that the training termination criteria are not satisfied, the system may return to 408. If the determination at 414 is that the training termination criteria are satisfied, the system may end the training process 400 at 416.

Figure 5:
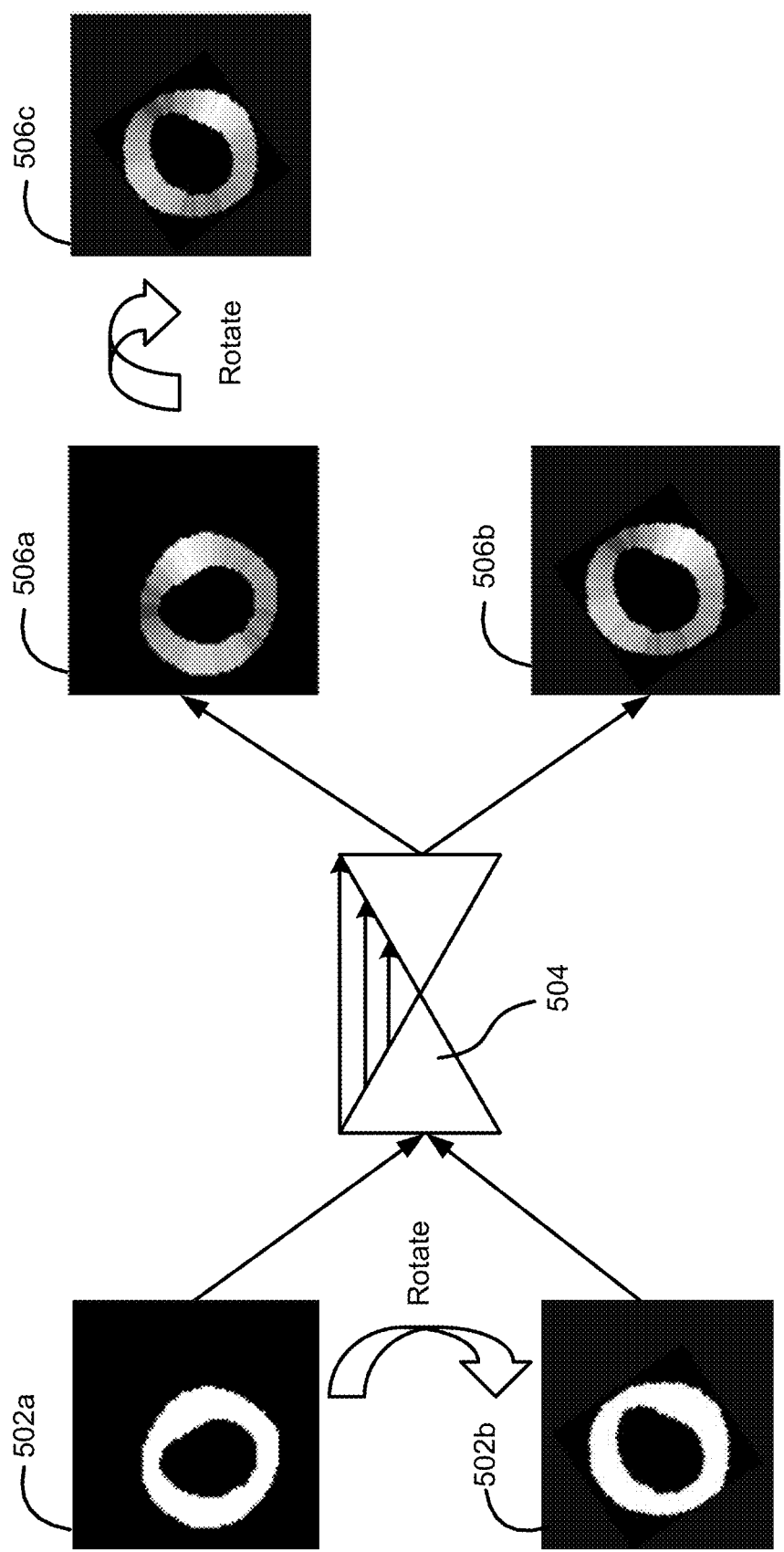
FIG. 5 is simplified block diagram illustrating an example of training data augmentation.

The data used to train a neural network system as described herein may be augmented to improve the system's performance, ability and robustness. The augmentation may be performed, for example, by rotating one or more of the training images or segmentations (e.g., by 90, 180, or 270 degrees, or via a random rotation), by flipping one or more of the training images or segmentations in the vertical and/or horizontal directions, by moving one or more of the training images or segmentations along the x-axis and/or y-axis (e.g., translation), etc. FIG. 5 shows an example of training data augmentation via image rotation. As shown, in addition to receiving a first visual representation 502a and processing the visual representation via a neural network 504 (e.g., the ANN 104a or ANN 104b) to obtain a first thickness estimation 506a, the neural network system may also receive a second visual representation 502b that is a rotated version of the visual representation 502a (e.g., by a degree of N). The second visual representation 502b may also be processed via the neural network 504 to obtain a second thickness estimation 506b. Since the visual representation 502b has been rotated by N degrees from the visual representation 502a, the second thickness estimation 506b is also expected to have been rotated N degrees from the first thickness estimation 506a and be consistent with a rotated estimation 506c. Accordingly, the neural network system may be further trained to optimize its parameters utilizing the additional visual representation 502b and by minimizing the difference between the thickness predictions 506b and 506c.

The examples provided thus far have been illustrated using 2D images or 2D segmentations. But the systems, methods and instrumentalities described in the examples may also be used to predict the thickness of an anatomical structure based on 3D images or 3D segmentations of the anatomical structure, and in some implementations, based further on temporal information associated with the images or segmentations.

Figure 6:
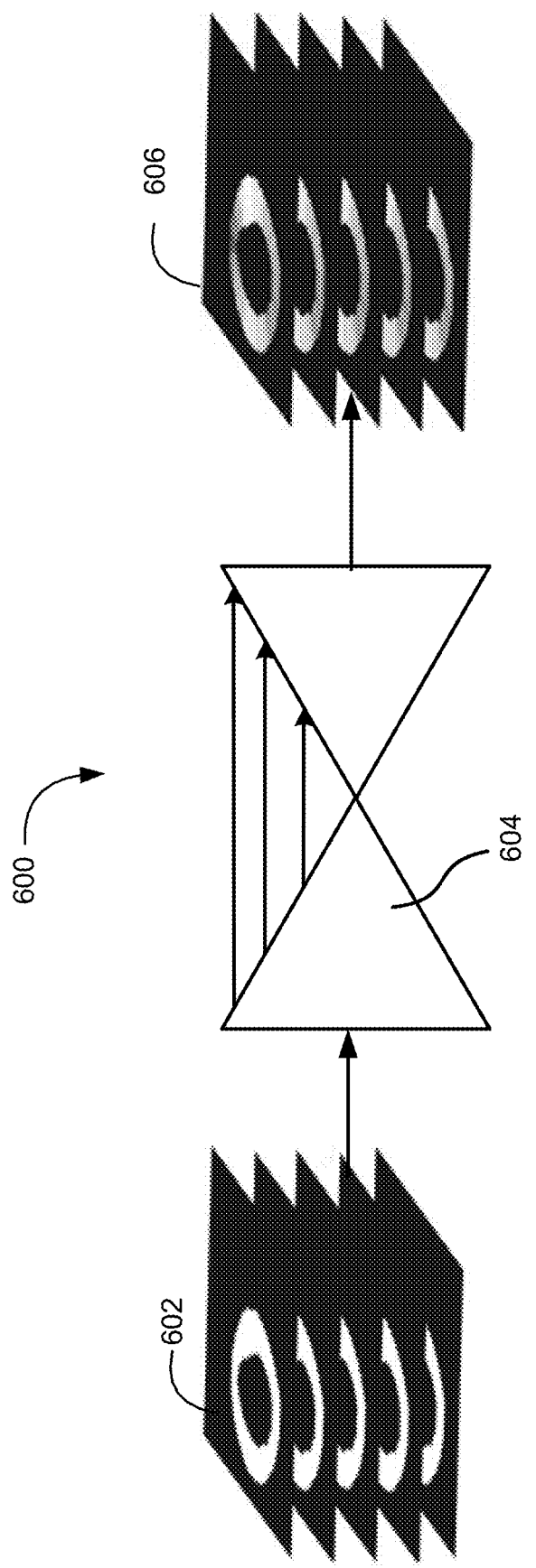
FIG. 6 is simplified block diagram illustrating an example neural network system for performing 3D thickness prediction.

FIG. 6 illustrates an example neural network system 600 that may be used to perform 3D thickness prediction. As shown, the neural network system 600 may treat a 3D visual representation 602 of an anatomical structure as a stack of 2D images or segmentation masks. The 3D visual representation 602 may include a 3D image (e.g., captured using a stereo camera) or a 3D segmentation of the anatomical structure derived based on the 3D image. The neural network system 600 may comprise a 3D artificial neural network 604 such as a 3D convolutional neural network trained to receive the visual representation 602 and extract features from the 3D visual representation based on keypoints and/or 3D spatial location information captured in the visual representation. For example, the 3D artificial neural network 604 may comprise a plurality of convolutional layers and each of the convolutional layers may include multiple 3D filters (e.g., 3D kernels) that not only have width and height dimensions but also a depth dimension. As such, the convolution operation of the 3D artificial neural network 604 may involve sliding the kernels in the width, height and depth directions to extract features from the visual representation 602 and produce a 3D volume as a result of the convolution operation. Based on the features extracted from the visual representation 602, the 3D artificial neural network 604 may estimate a thickness of the anatomical structure and generate an indication 606 of the thickness. The indication 606 may be, for example, in the form of a stack of color-coded or shaded images or segmentations in which each color or shade may represent a respective thickness of the anatomical structure, e.g., at one or more pixel positions of the images.

The 3D artificial neural network 604 may be trained using the techniques and/or training data described herein, e.g., in similar manners as the training of the ANNs 104a and 104b described above. For instance, the training of the 3D artificial neural network 604 may also utilize ground truth information derived by solving a partial differential equation such as Laplace's equation, as illustrated in FIG. 2. And a similar loss function such as an MSE function or a L1 or L2 norm as described herein may be used to guide the training.

Figure 7:
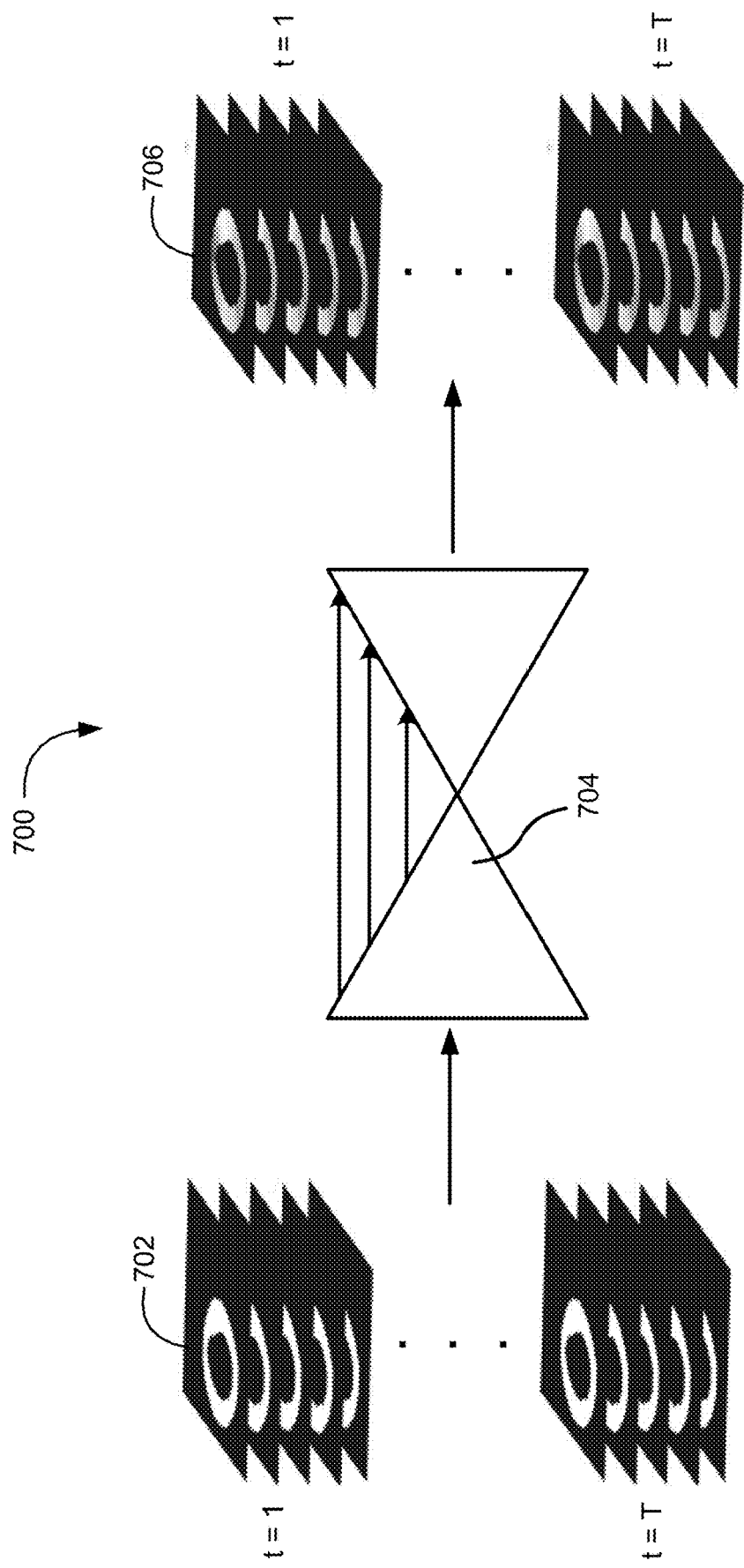
FIG. 7 is simplified block diagram illustrating an example neural network system for performing thickness prediction based on a sequence of segmentation masks.

The neural network systems described herein (e.g., the neural network systems 100a and 100b of FIG. 1 and/or the neural network system 500 of FIG. 5) may also be trained to predict the thickness of an anatomical structure based on a sequence of 2D or 3D images or a sequence of 2D or 3D segmentations. FIG. 7 illustrates an example of performing thickness prediction based on a sequence of 3D segmentation masks. In the example, a neural network system 700 may be configured to receive an input 702 that includes a sequence of segmentation masks corresponding to different points in time (e.g., t=1 to t=T). Such a timed sequence of segmentation masks may be derived from various data sources including, for example, a cine cardiac movie that depicts the movement of the myocardium in multiple frames along a time axis. As such, the sequence of segmentation masks may capture not only visual features of the anatomical structure, but also temporal correlation between adjacent frames of the anatomical structure that may be explored to improve the prediction accuracy of the neural network system 700.

The neural network system 700 may include an artificial neural network 704 (e.g., a CNN) trained to extract features and temporal correlation from the sequence of segmentation masks 702 and predict a thickness of the anatomical structure based on the extracted information. The prediction may be provided, for example, via an indication 706 that may be in the form of a sequence of color-coded or shaded segmentation masks corresponding to the input 702. The training of the artificial neural network 704 may be conducted using the techniques and/or training data described herein (e.g., based on ground truth data derived from Laplace's equation and an MSE or L1/L2 loss function). The training may utilize the temporal correlation between adjacent frames of the input sequence to improve the accuracy of the prediction results (e.g., a thickness map may be predicted frame by frame and utilizing the correlation information between the frames). For instance, since visual representations of the anatomical structure in two adjacent frames are expected to be very similar to each other, the respective thickness values estimated for the two frames can also be expected to be close to each other. Therefore, the training of the artificial neural network 704 may further consider (e.g., in addition to the MSE or L1/L2 loss function described herein) a temporal consistency loss that represents a difference between predicted thickness values for the two adjacent frames and optimize the parameters of the neural network 704 by forcing the temporal consistency loss to be below a certain threshold (e.g., a configurable threshold).

Figure 8:
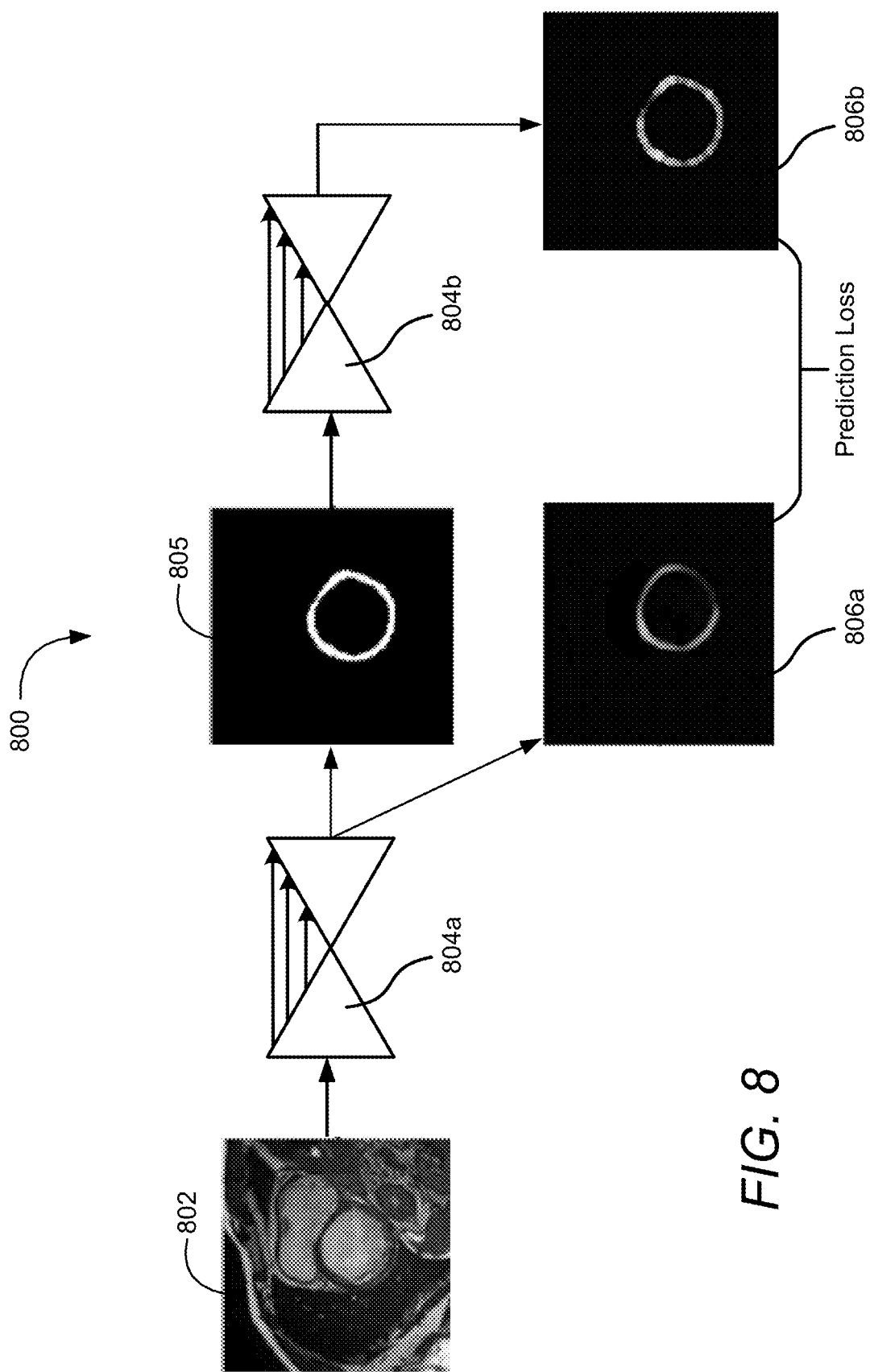
FIG. 8 is a simplified block diagram illustrating an example neural network system capable of performing both segmentation and thickness prediction.

The image-based thickness prediction techniques described herein may be closely related to those utilized for image segmentation because the image features (e.g., shape-related features) extracted and analyzed to accomplish an image segmentation task may also be used to accomplish a thickness prediction task (e.g., the shape information may be shared between the two tasks). Accordingly, a neural network system may be configured and trained to perform both segmentation and thickness estimation for an anatomical structure based on an image of the anatomical structure. FIG. 8 is a diagram illustrating such a multi-tasking neural network system 800.

As shown in FIG. 8, the neural network system 800 may include a neural network 804a that may be a convolutional neural network (CNN) as described herein. The neural network 804a may be configured to receive an image 802 of the anatomical structure (e.g., the myocardium) and extract features from the image 802 by performing one or more convolutional operations on the image. The features extracted from the image 802 may be used by the neural network 804a to generate a segmentation mask 805 of the anatomical structure, for example, utilizing techniques disclosed in commonly assigned U.S. patent application Ser. No. 16/905,115, filed Jun. 18, 2020, entitled "Systems and Methods for Image Segmentation," the disclosure of which has been incorporated herein by reference in its entirety. Since at least a portion of the features extracted from the image 802 may also be relevant to predicting the thickness of the anatomical structure, the neural network 804a may be further configured to generate an indication 806a of the thickness of the anatomical structure based on all or a subset of the features extracted from the image 802.

The neural network 804a may be configured with respective output layers and/or activation functions for performing the segmentation and thickness prediction tasks. For example, a first output layer of the neural network 804a may be associated with generating the segmentation mask 805 and that output layer may be assigned a softmax activation function. A second output layer of the neural network 804a may be associated with generating the thickness prediction 806a and that output layer may be assigned a non-linear or linear activation function. During training of the neural network 804a, different loss functions may be used for performing the segmentation task and the thickness prediction task, respectively. For example, the loss function for segmentation-related training may be based on softmax cross entropy while that for thickness prediction-related training may be based on L2 norm, L1 norm and/or L2 norm together with L1 norm.

The training of the neural network system 800 (e.g., the neural network 804a) may be guided by a neural network 804b that is pre-trained to generate a thickness map of the anatomical structure based on a segmentation mask of the anatomical structure. The neural network 804b may be pre-trained using the techniques described herein, for example, by providing segmentation masks at an input of the neural network 804b and using ground truth obtained from solving a partial differential equation to optimize the parameters of the neural network 804b (e.g., similar to the training of the neural network system 100a shown in FIG. 1). Once trained, the neural network 804b may act as a teacher network (e.g., with fixed parameters) during the training of the neural network system 800. For example, the neural network 804b may be configured to receive the segmentation mask 805 estimated by the neural network 804a and predict a thickness map 806b of the anatomical structure that may be used as pseudo ground truth to correct the thickness prediction 806a produced by the neural network 804a. Hence, using the guidance provided by the neural network 804b, the training of the neural network system 800 (e.g., the neural network 804a) for both segmentation and thickness prediction purposes may be conducted in an end-to-end manner with an objective to minimize the difference between the thickness prediction 806a made by the neural network 804a and the pseudo ground truth 806b produced by the neural network 804b. For instance, in the example shown in FIG. 8, an image may be received at the input and a thickness map may be produced at the output. As such, the neural network 804a may be trained to learn the image-to-segmentation and segmentation-to-thickness tasks together (e.g., as opposed to learning them separately in some embodiments).

Figure 9:
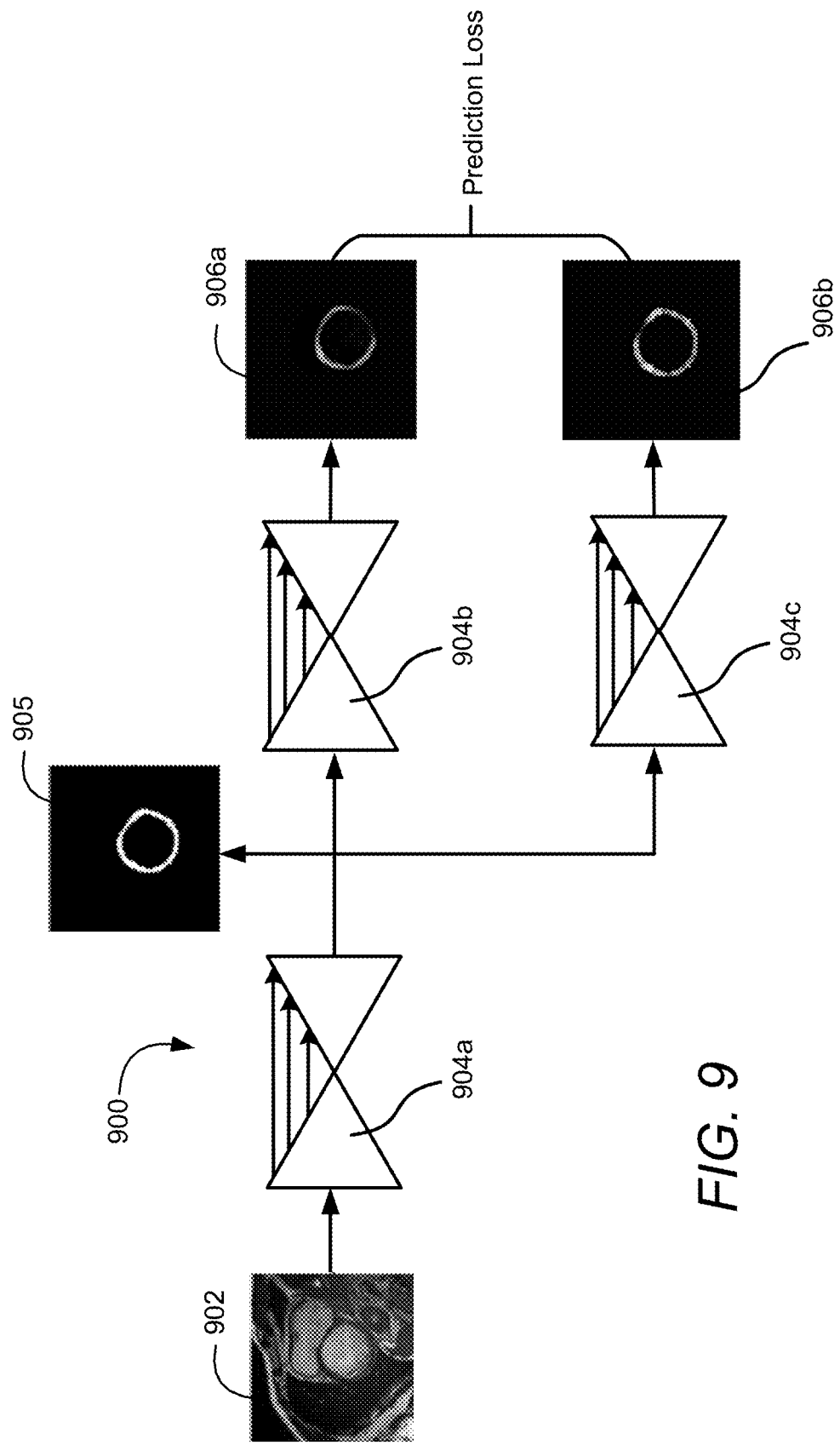
FIG. 9 is a simplified block diagram illustrating another example neural network system capable of performing both segmentation and thickness prediction.

FIG. 9 is another diagram illustrating a multi-tasking neural network system 900 that may be configured and trained to perform both segmentation and thickness prediction tasks relating to an anatomical structure such as the myocardium. The neural network system 900 may include a first neural network 904a and a second network 904b. The neural network 904a and/or the neural network 904b may include a convolutional neural network (CNN) as described herein. The neural network 904a may be configured to receive an image 902 of the anatomical structure and generate a segmentation mask 905 of the anatomical structure, for example, utilizing techniques disclosed in commonly assigned U.S. patent application Ser. No. 16/905,115, filed Jun. 18, 2020, entitled "Systems and Methods for Image Segmentation," the disclosure of which has been incorporated herein by reference in its entirety. The neural network 904b may be configured to receive the segmentation mask 905 generated by the neural network 904a and produce a thickness prediction 906a, for example, based on features extracted from the segmentation mask (e.g., similar to the neural network systems 100a shown in FIG. 1).

The training of the neural network system 900 (e.g., the neural networks 904a and 904b) may be guided by a neural network 904c that is pre-trained to generate a thickness map of the anatomical structure based on a segmentation mask of the anatomical structure. The neural network 904c may be pre-trained using the techniques described herein, for example, by providing segmentation masks at an input of the neural network 904c and using ground truth obtained from solving a partial differential equation to optimize the parameters of the neural network 904c (e.g., similar to the training of the neural network system 100a shown in FIG. 1). Once trained, the neural network 904c may act as a teacher network (e.g., with fixed parameters) during the training of the neural network system 900. For example, the neural network 904c may be configured to receive the segmentation mask 905 estimated by the neural network 904a and predict a thickness map 906b of the anatomical structure that may be used as pseudo ground truth to correct the thickness prediction 906a produced by the neural network 904b. Hence, using the guidance provided by the neural network 904c, the training of the neural network system 900 (e.g., the neural networks 904a and 904b) for both segmentation and thickness prediction purposes may be conducted in an end-to-end manner, for example, with an objective of minimizing the difference between the thickness prediction 906a made by the neural network 904b and the pseudo ground truth 906b produced by the neural network 904c. For instance, in the example shown in FIG. 9, an image may be received at the input and a thickness map may be produced at the output. As such, the neural networks 904a and 904b may be trained together (e.g., as opposed to being trained separately in some embodiments).

The neural networks 904a and 904b may be configured with respective output layers and/or activation functions for performing the segmentation and thickness prediction tasks. For example, the neural network 904a may include a logit layer and output a vector z. Based on such an output, the input to the teacher network 904c may be represented by argmax(z), which may correspond to a segmentation mask. The input to the neural network 904b may be represented by softmax(z), which may correspond to a probability map (e.g., since a softmax activation function is differential). As such, the neural network 904a may use softmax cross entropy as its loss function during the training, and the neural network 904b may use a L2 norm, L1 norm or L2 norm with L1 norm as its loss function during the training.

In examples, the input to the neural network 904b may be represented by softmax(z) with a temperature, e.g., as shown below:

$$q_i = \frac{\exp(z_i/T)}{\sum_j \exp(z_j/T)}$$

where $z_i$ may represent a logit value, $q_i$ may be a softmax value or probability, and T may be a temperature parameter. A higher T may produce a softer distribution and a lower T may produce a shaper distribution. The temperature parameter T may be fixed and/or annealed using a schedule strategy during training (e.g., T may have a fixed value during an inference stage).

Figure 10:
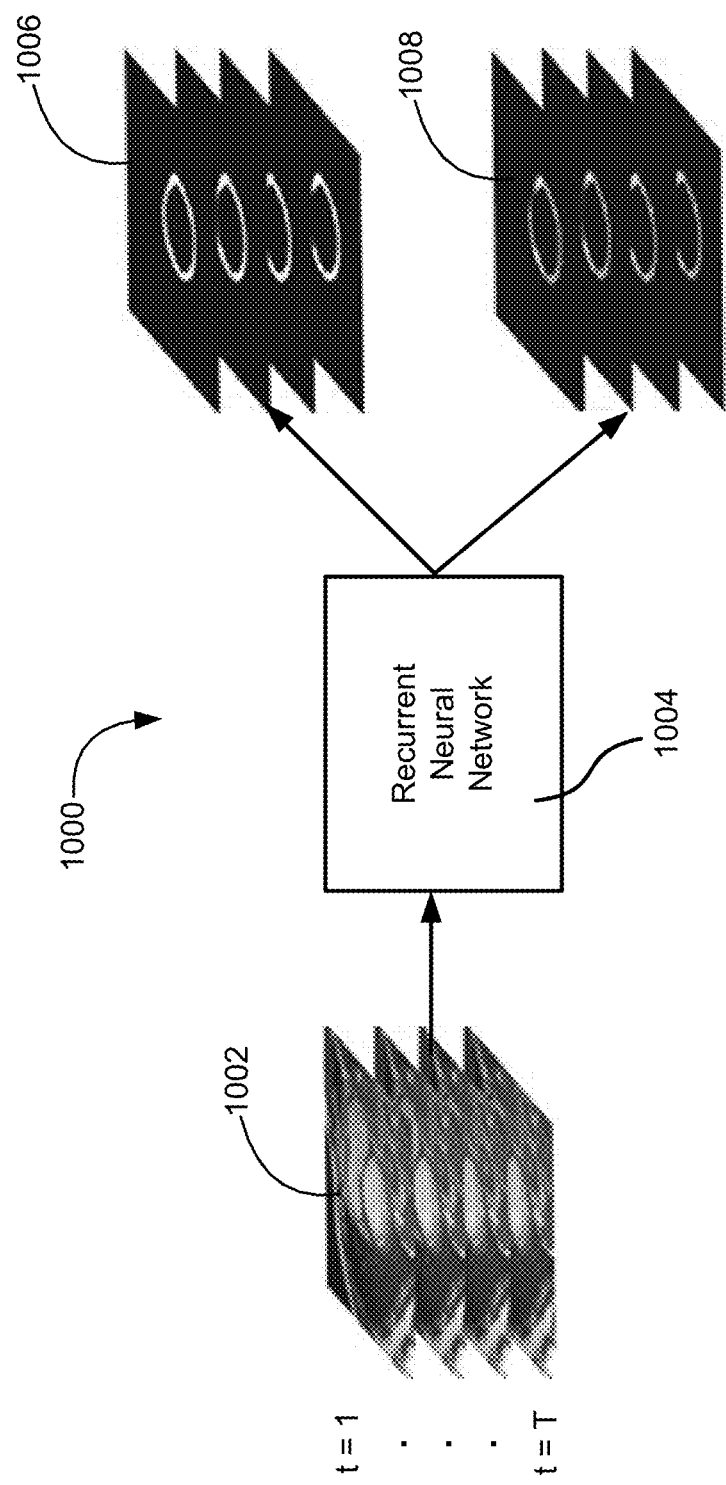
FIG. 10 is a simplified block diagram illustrating an example neural network system capable of performing both segmentation and thickness prediction based on a sequence of images.

The multi-tasking neural network systems described herein (e.g., the neural network system 800 of FIG. 8 or the neural network system 900 of FIG. 9) may also be configured and trained to process a sequence of 2D/3D images. FIG. 10 shows an example of such a system 1000. As shown, the input to the neural network system 1000 may include a sequence of images 1002 of an anatomical structure (e.g., the myocardium) and the output of the neural network system 1000 may include a sequence segmentation mask 1006 for the anatomical structure as well as a sequence of thickness predictions 1008 for the anatomical structure. The sequence of images 1002 may be correspond to different points in time (e.g., t=1 to t=T) and may be derived from a data source such as a cine cardiac movie that depicts the movement of the myocardium in multiple frames along a time axis. As such, the neural network system 1000 may include an artificial neural network 1004 that is trained to not only perform the segmentation and thickness prediction tasks as described herein (e.g., similar to the neural network system 800 or 900), but also to explore the temporal correlation between adjacent frames of the sequence of images 1002 to improve the performance of the neural network system 1000. For example, the artificial neural network 1004 may include a recurrent neural network (RNN) or a bidirectional RNN configured to capture the temporal context information of the sequence of images 1002 in the RNN's internal state and utilize the temporal context information to enforce temporal consistency among prediction results associated with the sequence of images. In examples, a temporal consistency loss may be added to facilitate the training of the artificial neural network 1004 (e.g., in addition to the segmentation and thickness prediction related loss functions described herein), and the parameters of the neural network 1004 may be further optimized by forcing the temporal consistency loss to be below a certain threshold (e.g., a configurable threshold).

Figure 11:
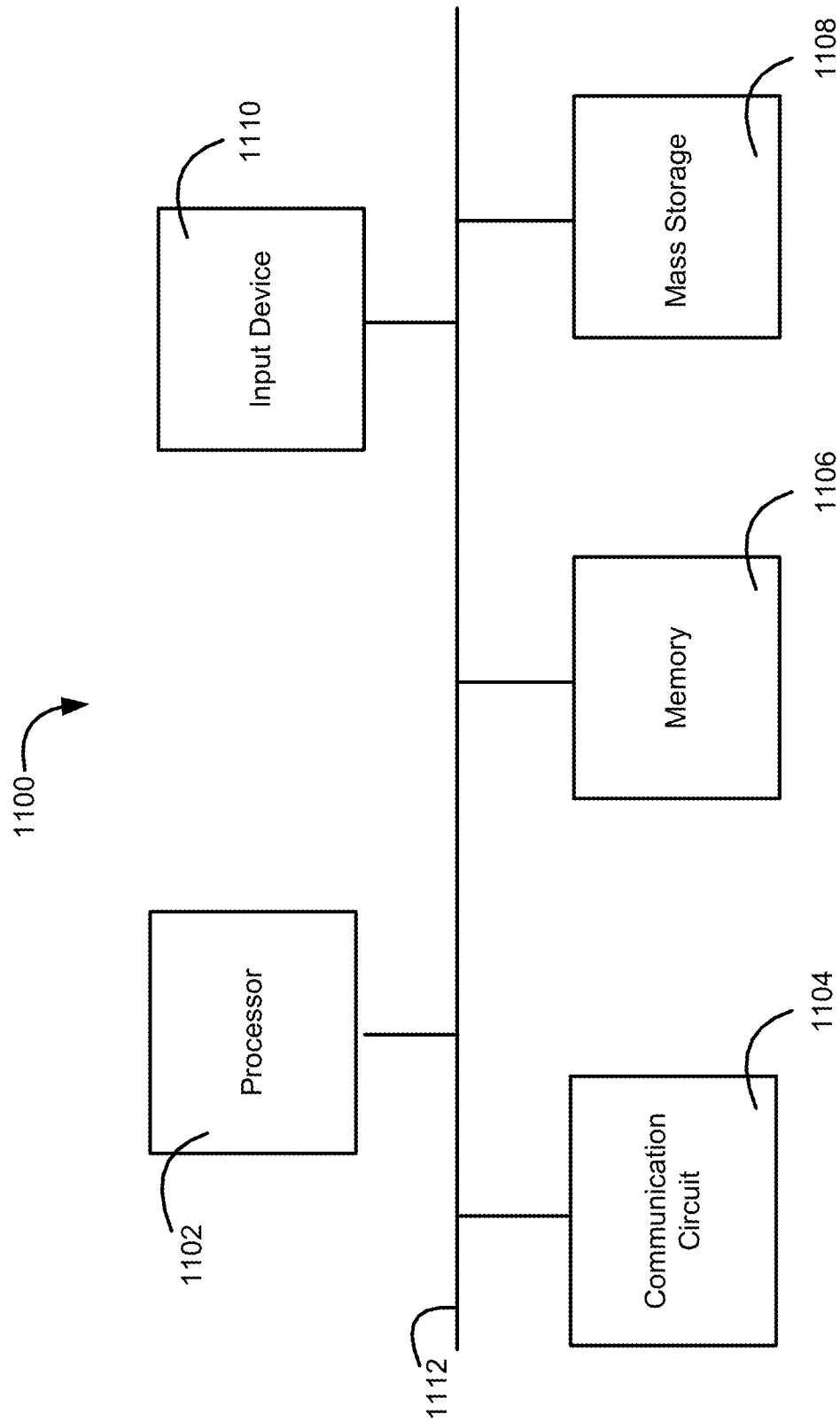
FIG. 11 is a simplified block diagram illustrating an example neural network system as described herein.

The neural network systems described herein may be implemented using one or more processors, one or more storage devices, and/or other suitable accessory devices such as display devices, communication devices, input/output devices, etc. FIG. 11 is a block diagram illustrating an example neural network system 1100 as described herein. As shown, the neural network system 1100 may include a processor 1102 configured to implement the one or more artificial neural networks described herein. The processor 1102 may be a central processing unit (CPU), a graphics processing unit (GPU), a microcontroller, a reduced instruction set computer (RISC) processor, application specific integrated circuits (ASICs), an application-specific instruction-set processor (ASIP), a physics processing unit (PPU), a digital signal processor (DSP), a field programmable gate array (FPGA), or any other circuit or processor capable of executing the functions described herein. The neural network system 1100 may further include a communication circuit 1104, a memory 1106, a mass storage device 1108, an input device 1110, and/or a communication link 1112 (e.g., a communication bus) over which the one or more components shown in FIG. 11 may exchange information. The communication circuit 1104 may be configured to transmit and receive information utilizing one or more communication protocols (e.g., TCP/IP) and one or more communication networks including a local area network (LAN), a wide area network (WAN), the Internet, a wireless data network (e.g., a Wi-Fi, 3G, 4G/LTE, or 5G network). The memory 1106 may include a storage medium configured to store machine-readable instructions that, when executed, cause the processor 1102 to perform one or more of the functions described herein including, e.g., implementing the one or more neural networks described herein. Examples of the machine-readable medium may include volatile or nonvolatile memory including but not limited to semiconductor memory (e.g., electrically programmable read-only memory (EPROM), electrically erasable programmable read-only memory (EEPROM)), flash memory, and/or the like. The mass storage device 1108 may include one or more magnetic disks such as one or more internal hard disks, one or more removable disks, one or more magneto-optical disks, one or more CD-ROM or DVD-ROM disks, etc., on which instructions and/or data may be stored to facilitate the operation of the processor 1102. The input device 1110 may include a keyboard, a mouse, a voice-controlled input device, a touch sensitive input device (e.g., a touch screen), and/or the like for receiving user inputs to the neural network system 1100.

It should be noted that the neural network system 1100 may operate as a standalone device or may be connected (e.g., networked or clustered) with other computation devices to perform the functions described herein. And even though only one instance of each component is shown in FIG. 11, a skilled person in the art will understand that the neural network system 1100 may include multiple instances of one or more of the components shown in the figure. Furthermore, although the examples are described herein with reference to various types of neural networks, various types of layers, and/or various tasks being performed by certain types of neural networks or layers, those references are made merely for illustration purposes and not meant to limit the scope of the disclosure. In addition, the operation of the example neural network system is depicted and described herein with a specific order. It should be appreciated, however, that these operations may occur in various orders, concurrently, and/or with other operations not presented or described herein. And not all operations that the neural network system is capable of performing are depicted and described herein, and not all illustrated operations are required to be performed by the system.

While this disclosure has been described in terms of certain embodiments and generally associated methods, alterations and permutations of the embodiments and methods will be apparent to those skilled in the art. Accordingly, the above description of example embodiments does not constrain this disclosure. Other changes, substitutions, and alterations are also possible without departing from the spirit and scope of this disclosure. In addition, unless specifically stated otherwise, discussions utilizing terms such as "analyzing," "determining," "enabling," "identifying," "modifying" or the like, refer to the actions and processes of a computer system, or similar electronic computing device, that manipulates and transforms data represented as physical (e.g., electronic) quantities within the computer system's registers and memories into other data represented as physical quantities within the computer system memories or other such information storage, transmission or display devices.

It is to be understood that the above description is intended to be illustrative, and not restrictive. Many other implementations will be apparent to those of skill in the art upon reading and understanding the above description. The scope of the disclosure should, therefore, be determined with reference to the appended claims, along with the full scope of equivalents to which such claims are entitled.

What is claimed is:

1. A neural network system comprising one or more processors and one or more storage devices, the one or more storage devices configured to store instructions that, when executed by the one or more processors, cause the one or more processors to:
   receive a visual representation of an anatomical structure, wherein the visual representation comprises an image depicting the anatomical structure;
   extract a plurality of features from the visual representation;
   generate a segmentation mask for the anatomical structure using a machine-learned segmentation model, wherein the segmentation model is trained to generate the segmentation mask based on the plurality of features extracted from the visual representation of the anatomical structure; and
   predict a thickness of the anatomical structure using a machine-learned thickness prediction model, wherein the thickness prediction model is trained to map the thickness of the anatomical structure to the plurality of features extracted from the visual representation of the anatomical structure and wherein the thickness prediction model is learned based on ground truth information derived using a partial differential equation.

2. The neural network system of claim 1, wherein the partial differential equation comprises Laplace's equation.

3. The neural network system of claim 2, wherein, when executed by the one or more processors, the instructions cause the one or more processors to implement a neural network pre-trained to learn the thickness prediction model and wherein the pre-training of the neural network comprises:
   the neural network receiving a training image or a training segmentation mask associated with the anatomical structure;
   the neural network predicting a first thickness of the anatomical structure based on features extracted from the training image or the training segmentation mask;
   the neural network comparing the first predicted thickness with a ground truth thickness derived by solving Laplace's equation between two surfaces of the anatomical structure in the training image or the training segmentation mask; and
   the neural network adjusting its parameters based on a difference between the first predicted thickness and the ground truth thickness.

4. The neural network system of claim 3, wherein the pre-training of the neural network further comprises:
   the neural network receiving a rotated version of the training image or training segmentation mask;
   the neural network predicting a second thickness of the anatomical structure based on features extracted from the rotated version of the training image or training segmentation mask;
   the neural network obtaining a rotated version the ground truth thickness;
   the neural network comparing the second predicted thickness with the rotated version of the ground truth thickness; and
   the neural network further adjusting its parameters based on a difference between the second predicted thickness and the rotated version of the ground truth thickness.

5. The neural network system of claim 1, wherein, when executed by the one or more processors, the instructions cause the one or more processors to implement a neural network pre-trained to learn the segmentation model and the pre-training of the neural network comprises:

the neural network receiving a training image depicting the anatomical structure;

the neural network generating an estimated segmentation mask for the anatomical structure based on features extracted from the training image;

the neural network providing the estimated segmentation mask to a pre-trained thickness prediction network to obtain a first estimated thickness of the anatomical structure, the thickness prediction network pre-trained to generate the first estimated thickness based on a training set comprising segmentation masks of the anatomical structure and a ground truth derived using the partial differential equation;

the neural network generating a second estimated thickness of the anatomical structure based on at least a subset of the features extracted from the training image; and the neural network adjusting its parameters based on a loss function associated with the first estimated thickness and second estimated thickness.

6. The neural network system of claim 1, wherein, when executed by the one or more processors, the instructions cause the one or more processors to:

implement the segmentation model with a first neural network; and implement the thickness prediction model with a second neural network.

7. The neural network system of claim 6, wherein training of the first and second neural networks comprises:

the first neural network generating an estimated segmentation mask for the anatomical structure based on features extracted from a training image;

the first neural network providing the estimated segmentation mask to a pre-trained thickness prediction network to obtain a first estimated thickness of the anatomical structure, the thickness prediction network pre-trained to generate the first estimated thickness based on a training set comprising segmentation masks of the anatomical structure and a ground truth derived using the partial differential equation;

the second neural network generating a second estimated thickness of the anatomical structure based on the estimated segmentation mask; and the first and second neural networks adjusting their respective parameters based on a loss function associated with the first estimated thickness and the second estimated thickness.

8. The neural network system of claim 1, wherein the visual representation of the anatomical structure comprises an image of the anatomical structure or a segmentation mask associated with the anatomical structure.

9. The neural network system of claim 1, wherein the visual representation of the anatomical structure comprises a time-based sequence of images or segmentation masks associated with the anatomical structure and wherein, when executed by the one or more processors, the instructions cause the one or more processors to implement a neural network pre-trained to predict the thickness of the anatomical structure based on the time-based sequence of images or segmentation masks, the pre-training of the neural network comprising:

the neural network predicting a first thickness of the anatomical structure corresponding to a first image or a first segmentation mask; and the neural network predicting a second thickness of the anatomical structure corresponding to a second image or a second segmentation mask that is sequential in time to the first image or first segmentation mask, the second thickness predicted based on a temporal correlation between the first and second images or between the first and second segmentation masks.

10. The neural network system of claim 9, wherein the neural network comprises a recurrent neural network configured to encode the temporal correlation between the first and second images or between the first and second segmentation masks.

11. The neural network system of claim 1, wherein the visual representation of the anatomical structure comprises a two-dimensional visual representation or a three-dimensional visual representation of the anatomical structure.

12. The neural network system of claim 1, wherein the anatomical structure comprises a myocardium, a cortex or a cartilage.

13. A method implemented by a neural network system for estimating a thickness of anatomical structure, the method comprising:

receiving a visual representation of the anatomical structure, wherein the visual representation comprises an image depicting the anatomical structure;

extracting a plurality of features from the visual representation;

generating a segmentation mask for the anatomical structure using a machine-learned segmentation model, wherein the segmentation model is trained to generate the segmentation mask based on the plurality of features extracted from the visual representation of the anatomical structure; and predicting a thickness of the anatomical structure using a thickness prediction model, wherein the thickness prediction model is trained to map the thickness of the anatomical structure to the plurality of features extracted from the visual representation of the anatomical structure and wherein the thickness prediction model is derived based on ground truth information obtained using a partial differential equation.

14. The method of claim 13, wherein the partial differential equation comprises Laplace's equation.

15. The method of claim 14, wherein the ground truth information is derived by solving Laplace's equation between two surfaces of the anatomical structure depicted in a training image or a training segmentation mask of the anatomical structure.

16. The method of claim 13, wherein the visual representation of the anatomical structure comprises an image of the anatomical structure or a segmentation mask of the anatomical structure.

17. The method of claim 13, wherein the visual representation of the anatomical structure comprises a time-based sequence of images or segmentation masks associated with the anatomical structure, and wherein predicting the thickness of the anatomical structure using the thickness prediction model comprises:

predicting a first thickness of the anatomical structure corresponding to a first image or a first segmentation mask; and predicting a second thickness of the anatomical structure corresponding to a second image or a second segmentation mask that is sequential in time to the first image or first segmentation mask, wherein the second thickness is predicted based on a temporal correlation between the first and second images or the first and second segmentation masks.

18. The method of claim 13, wherein the visual representation of the anatomical structure comprises a two-dimensional visual representation or a three-dimensional visual representation of the anatomical structure.

* * * * *